US 7,226,601 B1

(12) United States Patent
Abrahmsen et al.

(10) Patent No.: US 7,226,601 B1
(45) Date of Patent: Jun. 5, 2007

(54) CONJUGATE BETWEEN A MODIFIED SUPERANTIGEN AND A TARGET-SEEKING COMPOUND AND THE USE OF THE CONJUGATE

(75) Inventors: Lars Abrahmsen, Bromma (SE); Per Bjork, Helsingborg (SE); Mikael Dohlsten, Lund (SE); Terje Kalland, Arese (IT)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 08/765,695

(22) PCT Filed: Jun. 7, 1995

(86) PCT No.: PCT/SE95/00681

§ 371 (c)(1),
(2), (4) Date: Jul. 25, 1997

(87) PCT Pub. No.: WO96/01650

PCT Pub. Date: Jan. 25, 1996

(30) Foreign Application Priority Data

Jul. 11, 1994 (SE) .................................... 9402430

(51) Int. Cl.
*C07K 16/46* (2006.01)
*C07K 19/00* (2006.01)
*A61K 39/395* (2006.01)

(52) U.S. Cl. .............................. 424/197.11; 424/183.1; 424/178.1; 424/182.1; 424/192.1; 424/193.1; 514/2; 514/885; 530/391.1; 530/391.7; 530/402

(58) Field of Classification Search ............. 424/178.1, 424/182.1, 192.1, 193.1, 197.11, 183.1; 514/2, 514/885; 530/391.1, 391.7, 402
See application file for complete search history.

(56) References Cited

U.S. PATENT DOCUMENTS

| 3,627,644 | A | 12/1971 | Okamoto et al. |
| 4,237,224 | A | 12/1980 | Cohen et al. |
| 4,268,434 | A | 5/1981 | Higerd et al. |
| 4,681,870 | A | 7/1987 | Balint, Jr. et al. |
| 4,699,783 | A | 10/1987 | Terman et al. |
| 4,980,160 | A | 12/1990 | Goldberg et al. |
| 5,091,091 | A | 2/1992 | Terman |

FOREIGN PATENT DOCUMENTS

| EP | 0355047 | 2/1990 |
| WO | 88/00263 | 1/1988 |
| WO | 9104053 | 4/1991 |
| WO | 91/10680 | 7/1991 |
| WO | 9201470 | 2/1992 |
| WO | 9301302 | 1/1993 |
| WO | 9314634 | 8/1993 |
| WO | 9324136 | 12/1993 |

OTHER PUBLICATIONS

Forsberg et al., Brit. J. Cancer, 85:129-136, 2001.*
Newton et al., The Journal of Immunol., 157:3988-3994, 1996.*
Letter of Aug. 27, 1998 to European Patent Office by Opponent David Terman vs. Proprietor Pharmacia & Upjohn AB re Opponent's Comments in Response to Invitation to File Observations on the Patentee's Submissions, re. Opposition to European Patent No. EP-B-444186 (90914564.1).
Todd et al., Toxic Shock Syndrome Associated with Phage-Group I Staphylococci Lancet 2: 116-120 (1978).
Shands et al., Toxic Shock Syndrome in Menstruating Woman: Association with Tampon Use and *Staphylococcus aureus* and Clinical Features in 52 Cases New Engl, J. Med. 303 1436-1441 (1980).
Fisher et al., Cardio-respiratory Failure in Toxic Shock Syndrome: Effect of Dobutamine Critical Care Medicine 13: 160-165 (1985).
Bergdoll et al., A New Staphylococcus Enterotoxin, Enterotoxin F, Associated with the Toxic Shock Syndrome *Staphylococcus aureus* Isolates Lancet 2 1017-1021 (1981).
Willoughby et al., The Toxic Shock Syndrome and Streptococcal Pyrogenic Exotoxins Ann. Int. Med. 98: 559 (1983).
Cone et al., Clinical and Bacteriological Observations of a Toxic Shock-Like Syndrome due to *Streptococcus pyrogenes* New Engl. J. Med. 317: 146-148 (1987).
Stevens et al., Severe Group A Streptococcal Infections Associated with a Toxic Shock-like Syndrome and Scarlet Fever Toxin A New Engl J. Med 32: 321: 1-7 (1989).
Schilievert, PM Staphylococcal Enterotoxin B and Toxic Shock Syndrome Toxin-1 are Significantly Associated with Non-Menstrual TSS Lancet 1: 1149-1150 (1986).
Johnson et al., Mol. Gen. Genet. 203, 354 to 356 (1986).
Borja et al., Biochemistry vol. 6, No. 5, pp. 1467 to 1473, 1967.
Elsberry et al., Hemodynamics of Staphylococcal B Enterotoxaemia and Other Types of Shock in Monkeys J. Applied Physiology 27 164-169.
Liu et al., Cardiovascular and Vomiting Responses to a Lethal Intravenous Dose of Staphyloenterotoxin A in Rhesus Monkeys J Med Primatol. 5: 353-359 (1976).
Eur. J. Immunogenetics 19: 181-285 (1992).
Acolla RJ et al., J. Exp. Med. 157: 1053-1058 (1983).
Kavathas et al., Gamma Ray-induced Loss of Expression of HLA and Glyoxalase I Alleles in Lymphoblastoid Cells Proc. Natl. Acad. Sci. USA 77: 4251-4255 (1980).
Acolla et al., J. Exp. Med. 162: 1117-1133 (1985).
Acolla et al., J. Exp. Med. 164: 369-374 (1986).
Acolla et al., Proc. Natl. Acad. Sci. USA 82: 5145-5149 (1985).

(Continued)

*Primary Examiner*—Ronald B. Schwadron
(74) *Attorney, Agent, or Firm*—Fulbright & Jaworski LLP

(57) ABSTRACT

A method for the treatment of a disease in a mammal by administering a therapeutically effective amount of a conjugate comprising a biospecific affinity counterpart and a peptide, wherein the peptide contains an amino acid sequence that is derived from staphylococcal enterotoxin A, binds to a Vβ of a T cell receptor, and has a D227A mutation so that the peptide has a modified ability to bind to MHC class II antigens.

2 Claims, 7 Drawing Sheets

OTHER PUBLICATIONS

Figure 1:
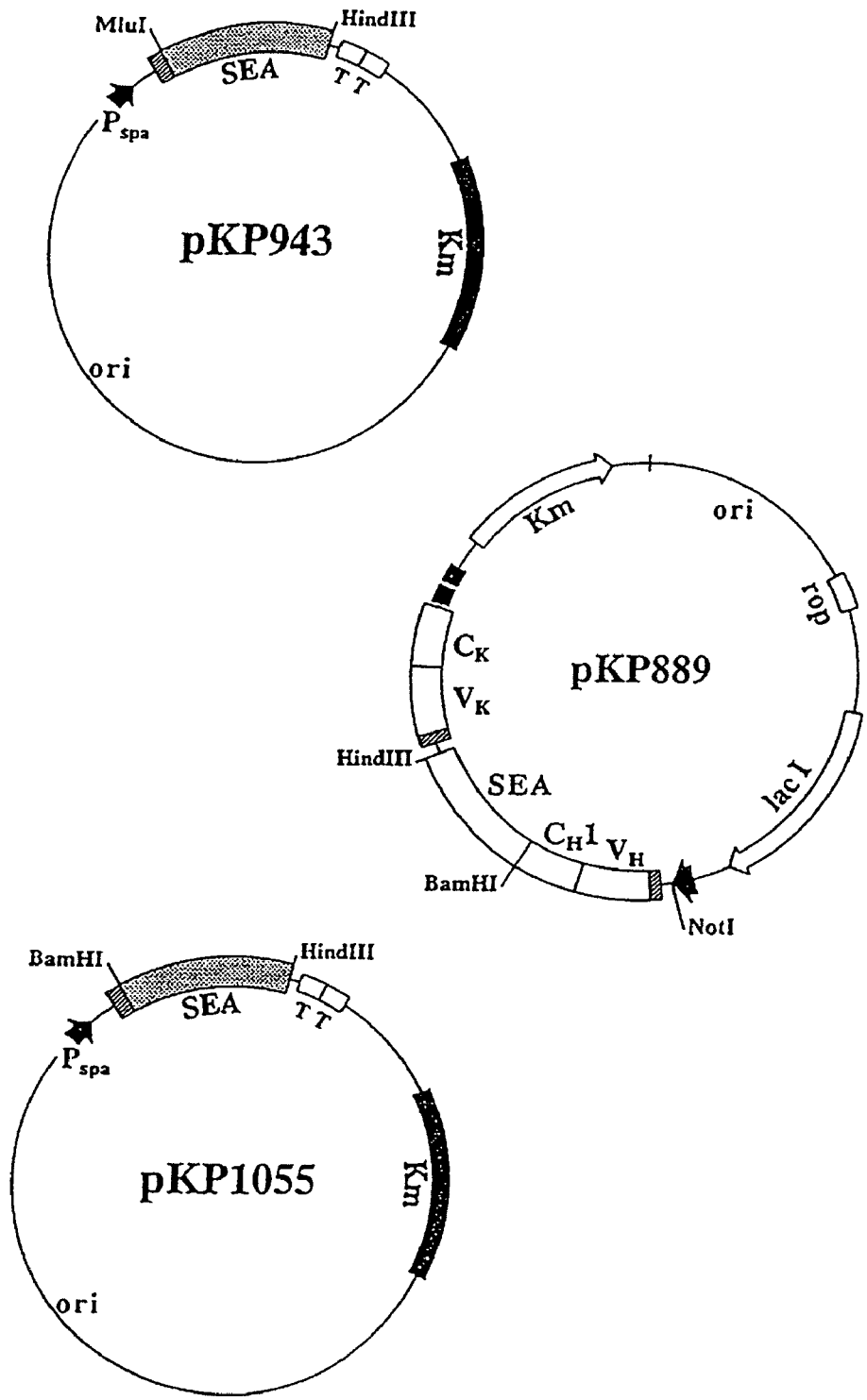
Figure 2:
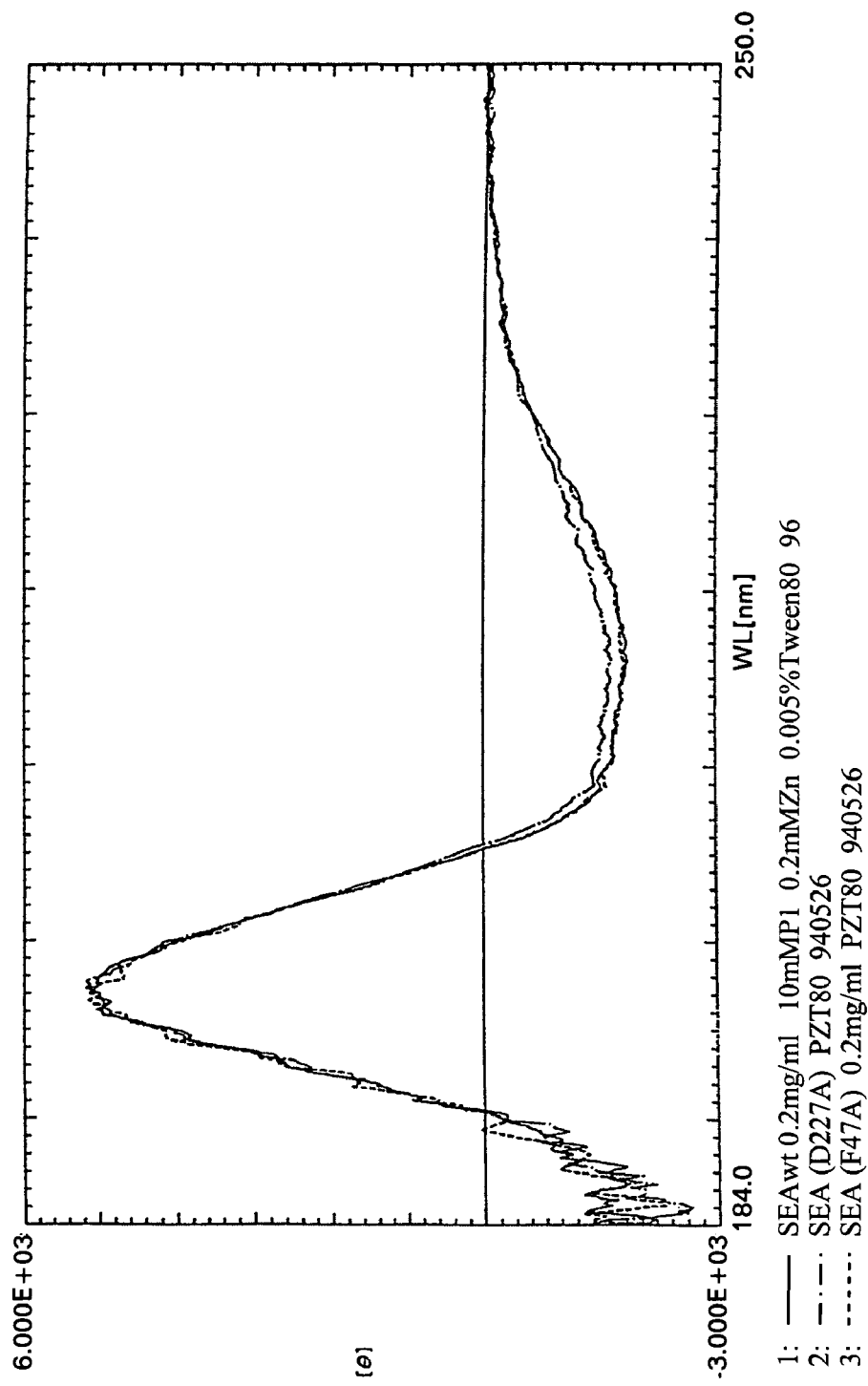
Figure 3:
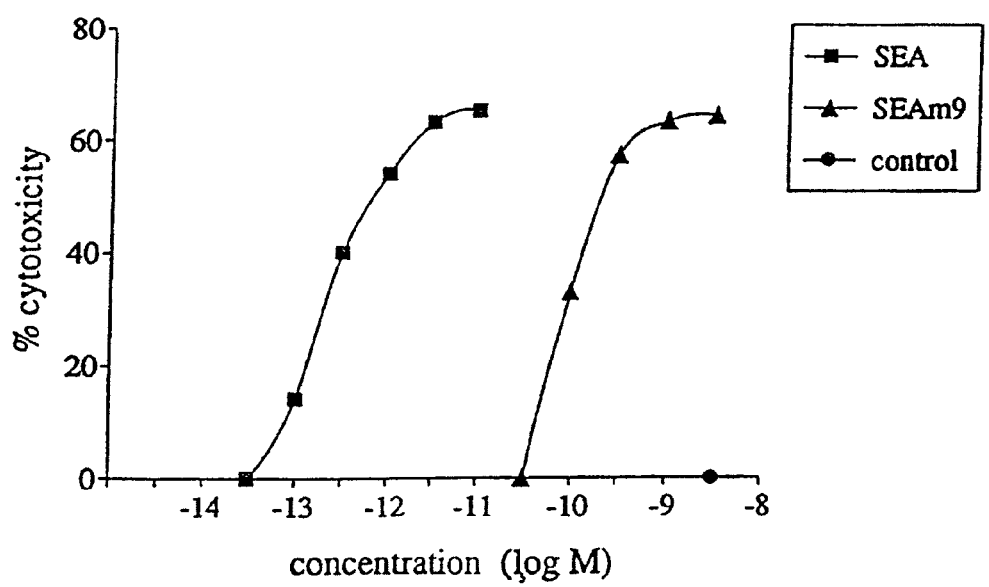
Figure 4:
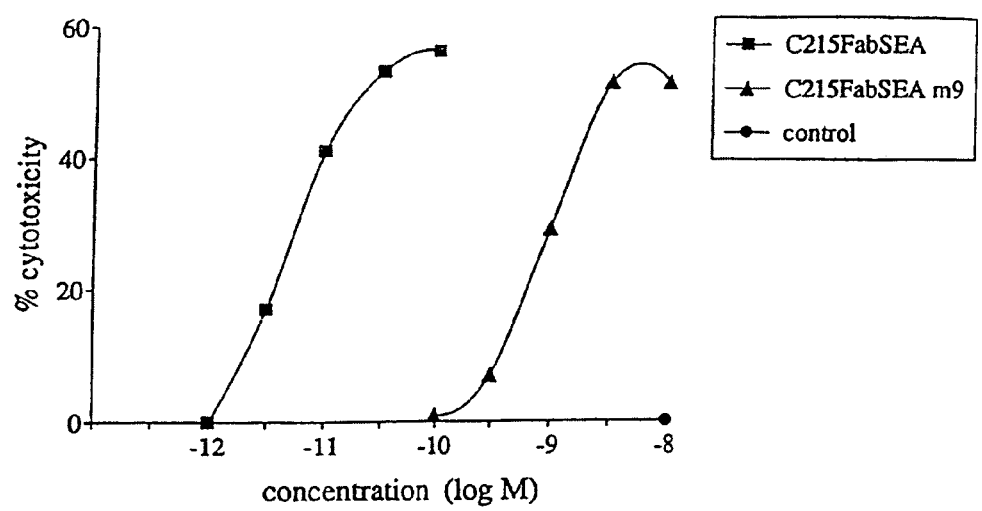

Shoemaker et al., Development of Human Tumour Cell Line Panels for use in Disease-Oriented Drug Screening in T. Hall editor Prediction of Response to Cancer Therapy Alan Liss N.Y. pp. 265-286 (1988).

Paull K.D. et al., J. Natl. Cancer Inst. 81: 1088-1092 (1989).

Alley M.C. et al., Cancer Res. 48: 589-601 (1988).

Scudiero D.A. et al., Cancer Res. 48: 4827-4833 (1988).

Developmental Therapeutics Program Division of Cancer Treatment, National Cancer Institute Proceedings of Workshop on "Selection, Characterisation and Quality Control of Human Tumour Cell Lines from the NCI's New Drug Screening Program" Bethesda, MD May 27-28, 1-73 (1987).

Boyd M.R. Status of NCI preclinical antitumour drug discovery screen in DeVita V.T., Hellman S., Rosenberg S.A., eds Cancer: Principles and Practice of Oncology Updates, vol. 3, No. 10, Lippincott, Philadelphia 1-12 (1989).

Rooney C., et al., J. Natl. Cancer Inst. (1986).

Sausville E.A. in Anticancer Drug Development Guide: Preclinical Screening, Clinical Trials and Approval B. Teicher editor, Human Press, Totowa, N.J.

D. Terman et al., "Preliminary Observations of the Effects on Breast Adenocarcinoma of Plasma Perfused Over Immobilized Protein A," New Eng. J. Med., 305:1195-1200 (1981).

F. Chu et al., "Purification and Characterization of Staphylococcal Enterotoxin A," Biochem., 5:3281 (1966).

M. Bergdoll et al., "Identification of a New Enterotoxin as Enterotoxin C," J. Bacteriol., 90:1481 (1965).

C. Borja and M. Bergdoll, "Purification and Partial Characterization of Enterotoxin C Produced by *Staphylococcus aureus* Strain 137," Biochem., 6:1467 (1967).

R. Avena and M. Bergdoll, "Purification and Some Physicochemical Properties of Enterotoxin C, *Staphylococcus aureus* Strain 361," Biochem., 6:1474 (1967).

E. Schantz et al., "Purification and Some Chemical and Physical Properties of Staphylococcal Enterotoxin A." Biochem., 11:360 (1972).

E Schantz et al., "Purification of Staphylococcal Enterotoxin B," Biochem., 4:1011 (1965).

H-C. Chang and M. Bergdoll, "Purification and Some Physicochemical Properties of Staphylococcal Enterotoxin D," Biochem., 18:1937 (1979).

C. Borja et al., "Purification and Some Physicochemical Properties of Staphylococcal Enterotoxin E," J. Biol. Chem., 247:2456 (1972).

M. Dayhoff (ed.), Data Section, *in Atlas of Protein Sequence Structure* 5:D227, National Biomedical Research Foundation, Washington, D.C. (1972).

I. Huang and M. Bergdoll, "The Primary Structure of Staphylococcal Enterotoxin B," J. Biol. Chem., 245:3493 (1970).

M. Bergdoll et al., "Enterotoxin Synthesis by the Staphylococci," *In Recent Advances in Staphylococcal Research* (W.W. Yotis, ed.), Ann. N.Y. Acad. Sci., 236:307.

J. Iandolo, "Genetic Analysis of Extracellular Toxins of *Staphylococcus aureus*," Ann. Rev. Microbiol., 43:375 (1989).

M. Bergdoll et al., "Staphylococcal Enterotoxin B, III. The Physicochemical Properties and the N—and C-Terminal Amino Acid Sequences," Arch. Biochem. Biophys., 112:104 (1965).

I. Huang et al., "Amino Acid Composition and Terminal Amino Acids of Staphylococcal Enterotoxin C," Biochem., 6:1480 (1967).

M. Bergdoll et al., "Chemistry of the Staphylococcal Enterotoxins," J. Agric. Food Chem., 22:9 (1974).

D. Blomster-Hautamaa et al., "Preparation of Toxic Shock Syndrome Toxin-1," Methods in Enzymology 165:37 (1988).

M. Bergdoll et al., "Identification of Enterotoxin E," Infect. Immun., 4:593 (1971).

M. Bergdoll, "Enterotoxins," *in Staphylococci and Staphylococci Infections* (C.S.F. Easmon and C. Adlam, eds.), pp. 559-598 (1983).

J. Freer and J. Arbuthnott, "Toxins of *Staphylococcus aureus*," Pharmac. Ther., 19:55 (1983).

L. Johnson et al., "Streptococcal Pyrogenic Exotoxin Type A (scarlet fever toxin) is related to *Staphylococcus aureus* Enterotoxin B," Mol. Gen. Genet., 203:354 (1986).

W. Pearson and D. Lipman, "Improved Tools for Biological Sequence Comparison," Proc. Nat'l. Acad. Sci. USA, 85:2444 (1988).

J. Lipman and W. Pearson, "Rapid and Sensitive Protein Similarity Searches," Sci., 227:1435 (1985).

C. Janeway, Jr. et al., "T-Cell Responses to Mls and to Bacterial Proteins that Mimic its Behavior," Immunol. Rev., 107:61-88.

J. Yagi et al., "Bacterial Proteins That Mediate the Association of a Defined Subset of T Cell Receptor:CD4 Complexes With Class II MHC," J. Immunol., 144:892-901.

H. Stewart et al., *in Atlas of Tumor Pathology*, Armed Forces Institute of Pathology, Washington, D.C., pp. 38, 355 (1959).

J. Kidd et al., "A Transplantable Rabbit Carcinoma Originating in a Virus-Induced Papilloma and Containing the Virus in Masked or Altered Form," J. Exp. Med., 71:813-838 (1940).

T. Maniatis et al., *Molecular Cloning: A Laboratory Manual*, Cold Spring Harbor Laboratory, New York (1982).

J. Betley and J. Mekalanos, "Nucleotide Sequence of the Type A Staphylococcal Enterotoxin Gene," J. Bacteriol., 170:34 (1987).

I. Huang et al., "Complete Amino Acid Sequence of Staphylococcal Enterotoxin A," J. Biol. Chem., 262:7006 (1987).

M. Betley et al., "Staphylococcal Enterotoxin A Gene is Associated With a Variable Genetic Element," Proc. Natl. Acad. Sci. USA 81:5179 (1984).

M. Gaskill and S. Khan, "Regulation of the Enterotoxin B Gene in *Staphylococcus aureus*," J. Biol. Chem., 263:6276 (1988).

C. Jones and S. Khan, "Nucleotide Sequence of the Enterotoxin B Gene from *Staphylococcus aureus*," J. Bacteriol., 166:29 (1986).

I. Huang and M. Bergdoll, "The Primary Structure of Staphylococcal Enterotoxin B," J. Biol. Chem., 245:3518 (1970).

G. Bohach and P. Schlievert, "Expression of Staphylococcal Enterotoxin $C_1$ in *Escherichia coli*," Infect. Immun., 55:428 (1987).

G. Bohach and P. Schlievert, "Nucleotide Sequence of the Staphylococcal Enterotoxin $C_1$ Gene and Relatedness to Other Pyrogenic Toxins," Mol. Gen. Genet., 209:15 (1987).

J. Couch et al., "Cloning and Nucleotide Sequence of the Type E Staphylococcal Enterotoxin Gene," J. Bacteriol., 170:2954 (1988).

B. Krieswirth et al., "The Toxic Shock Syndrome Exotoxin Structural Gene is Not Detectably Transmitted by a Prophage," Nature 305:709 (1983).

J. Cooney et al., "Molecular Cloning and Genetic Analysis of the Determinant for Gamma-Lysin, a Two-component Toxin of *Staphylococcus aureus*," J. Gen. Microbiol., 134:2179 (1988).

M. Freidman et al., "Induction of Mutants of *Staphylococcus aureus* 100 With Increased Ability to Product Enterotoxin A," J. Bacteriol., 106:289 (1971).

D. Terman, "Staphylococcal Protein A in Neoplastic Disease," J. Biol. Response Modifiers 3:316 (1984).

D. Terman and J. Bertram., "Antitumor Effects of Immobilized Protein A and Staphylococcal Products: Linkage Between Toxicity and Efficacy, and Identification of Potential Tumoricidal Reagent," Eur. J. Cancer Clin. Oncol., 21:1115 (1985).

D. Terman, "Immunoadsorbents in Autoimmune and Neoplastic Diseases," Plasma Ther. Transfus. Technol., 4:415 (1983).

D. Terman, "Protein A and Staphylococcal Products in Neoplastic Disease," CRC Crit. Rev. Oncol./Hematol., 4:103 (1985).

D. Terman, "Immobilized Enzymes and Cells," *in Methods in Enzymology*, vol. 137 (K. Mosbach, ed.), Academic Press, San Diego, pp. 496-515 (1988).

J. Mikoläšek, "Direct Evidence for Rejection of Tumour Allografts in *S. pyogenes* Toxins-Treated Mice Correlated with Antistreptolysin O Level in Serum," Neoplasma 19:507 (1972).

O. Shcheglovitova et al., Biol. Abstr., 84(5):AB-685, Ref. 48345 (1987); O.N. Shcheglovitova et al., Biol. Abstr., 88(8):AB-700, Ref. 87362 (1989); and O.N. Shcheglovitova et al., Biol. Abstr., 88(7):AB-639, Ref. 75810 (1989).

P. Garcia-Peñarrubia et al., "Selective Proliferation of Natural Killer Cells Among Monocyte-Depleted Peripheral Blood Mononuclear Cells as a Result of Stimulation with Staphylococcal Enterotoxin B," Infect. and Immun., 57:2057 (1989).

E. Carswell et al., "An Endotoxin-induced Serum Factor That Causes Necrosis of Tumors," Proc. Nat. Acad. Sci. USA 72:3666 (1975).

D. Fast et al., "Toxic Shock Syndrome-Associated Staphylococcal and Pyrogenic Toxins Are Potent Inducers of Tumor Necrosis Factor Production," Infect. Immun., 57:291 (1989).

C. Platsoucas et al., "Immunomodulation of Human Leukocytes by Staphylococcal Enterotoxin A: Augmentation of Natural Killer Cells and Induction of Suppressor Cells," Cellular Immunol., 97:371 (1986).

K. Newell et al., "In vivo T-cell Activation by Staphylococcal Enterotoxin B Prevents Outgrowth of a Malignant Tumor," Proc. Natl. Acad. Sci. USA 88:1074 (1991).

J. Kappler et al., "Vβ-Specific Stimulation of Human T Cells by Staphylococcal Toxins," Science 244:811-813 (1989).

H. Schrezenmeier and B. Fleischer, "Mitogenic Activity of Staphylococcal Protein A is Due to Contaminating Staphylococcal Enterotoxins," J. Immun. Meth., 105:133 (1987).

J. Sjöquist et al., "Protein A Isolated From *Staphylococcus aureus* After Digestion With Lysostaphin," Eur. J. Biochem., 29:572 (1972).

J. Balint, Jr. et al., "Detection, Isolation and Characterization of Staphylococcal Enterotoxin B in Protein A Preparations Purified by Immunoglobulin G Affinity Chromatography," J. Immun. Meth., 116:37 (1989).

Buelow et al., (1992), J. Immunol. 148:1-6.

Dohlsten et al., (1991), Proc. Natl. Acad. Sci. USA 88 9287-9291.

Dohlsten et al., (1994), Proc. Natl. Acad. Sci. USA 91;8945-8949.

Grossman, et al. (1991) J. Immunol. 147(10):3274-3281.

Hartwig, et al., (1993) Int. Immunol 5(8):869-875.

Hufnagle et al. (1991) Infect. Immun. 59 2126-2134.

Kappler et al. (1992) J. Exp. Med 175 387-396.

Kotzin et al. (1993) Adv. Immunol. 54 99-166.

Newell et al. (1991) Proc. Natl. Acad. Sci USA 88 1074-1078.

Jardetzky, Theodore S., et al. Three-dimensional structure of a human class II histocompatibility molecule complexed with superantigen; *Nature* vol. 368, p. 711-718 (1994).

Kim, Jongsun, et al. Toxic Shock Syndrome Toxin-1 Complexed with a Class II Major Histocompatibility Molecule HLA-DR1; *Science* vol. 266, p. 1870-1874 (1994).

\* cited by examiner

CONJUGATE BETWEEN A MODIFIED SUPERANTIGEN AND A TARGET-SEEKING COMPOUND AND THE USE OF THE CONJUGATE

Superantigens are primarily proteins of viral or bacterial origin and are capable of simultaneous binding to MHC class II antigens on mammalian cells and the T cell receptor Vβ chain. The binding leads to activation of T-lymphocytes and lysis of the MHC class II bearing cells. The moderate degree of polymorphism of the binding part of the Vβ chain causes a relatively large portion of the T-lymphocytes to be activated when contacted with a superantigen (in comparison with activation through normal antigen-processing).

Initially the superantigen concept was associated with various staphylococcal enterotoxins (SEA, SEB, $SEC_1$, $SEC_2$, SED, and SEE). Recently a new staphylococcal enterotoxin named SEH has been discovered (Keyong et al., J. Exp. Med. 180 (1994) 1675–1683). After the interest had been raised, further superantigens were discovered. Examples are Toxic Shock Syndrome Toxin 1 (TSST-1), Exfoliating Toxins (Exft) that are associated with scalded skin syndrome, Streptococcal Pyrogenic Exotoxin A, B and C(SPE A, B, and C), Mouse Mammary Tumor Virus Proteins (MMTV), Streptococcal M Proteins, Clostridial perfringens enterotoxin (CPET) among others. For a review of superantigens and their properties see Kotzin et al. (Adv. Immunol. 54 (1993) 99–166).

Pseudomonas exotoxin A has been looked upon as a functional superantigen because there are results indicating that this toxin may be processed intracellularly by accessory cells to fragments that are expressed on the cell surface with the ability to bind to the Vβ chain and a subsequent activation of T cells. (*Pseudomonas* exotoxin A. Legaard et al., Cell. Immunol. 135 (1991) 372–382).

Superantigens as such have been suggested for therapy of various diseases with curative effects being accomplished through a general activation of the immune system (Kalland et al., WO 9104053; Terman et al., WO 9110680; Terman et al., WO 9324136; Newell et al., Proc. Natl. Acad. Sci. USA 88 (1991) 1074–1078).

In connection with vaccines it has been suggested to use superantigens that have been mutated so as to lose their TCR binding ability (Kappler & Marrack, WO 9314634).

The mutation of superantigens has previously been described (Kappler & Marrack, WO 9314634; Kappler et al., J. Exp. Med. 175 (1992) 387–396; Grossman et al., J. Immunol. 147 (1991) 3274–3281; Hufnagle et al., Infect. Immun. 59 (1991) 2126–2134).

We ourselves have previously suggested to employ conjugates between a superantigen and an antibody for therapy in order to lyse cells that express the structure towards which the antibody is directed (Dohlsten et al., WO 9201470; Lando et al., Cancer Immunol. Immunother. 36 (1993) 223–228; Kalland et al., Med. Oncol. Tumor Pharmacother. 10 (1993) 37–47; Lando et al., J. Immunol. 150 (8 part 2) (1993) 114A (Joint Meeting of the American Association of Immunologists and the Clinical Immunology Society, Denver, Colo., USA, May 21–25 (1993)); Lando et al., Proc. Am. Assoc. Cancer Res. Annu. Meet. 33(O) (1992) 339 (Annual meeting of the American Association for Cancer Research, San Diego, Calif., USA, May 20–23 (1992)); Dohlsten et al., Proc. Natl. Acad. Sci. USA 88 (1991) 9287–9291). Diseases suggested to be treated have been cancers, viral infections, parasitic infestations, autoimmune diseases and other diseases associated with cells expressing disease-specific surface structures. The experimental work carried out so far has focused on conjugates containing recombinant SEA and various anti-cancer antibodies. The conjugates as such have had a somewhat reduced ability to bind MHC class II antigens compared to the non-conjugated form of the superantigen. It has not been determined if a decreased MHC class II antigen binding ability is beneficial or not for achieving an optimal lyse and an optimal therapeutic effect.

Immune therapy experiments with SEB chemically conjugated to a tumor specific anti-idiotype antibody have previously been described by Ochi et al., (J. Immunol. 151 (1993) 3180–3186).

During the prosecution of the priority application the Swedish Patent Office has additionally cited Buelow et al. (J. Immunol. 148 (1992) 1–6) that describes fusions between Protein A and fragments of SEB without emphasis of the MHC classs II binding or use of the fusion for cell killing; and Hartwig et al. (Int. Immunol. 5 (1993) 869–875) that describes mutations affecting MHC class II binding of the non-fused form of the superantigen streptococcal erythrogenic toxin A.

THE OBJECTIVES OF THE INVENTION

A first objective of the invention is to improve previously known superantigen-antibody conjugates with respect to general immune stimulation versus directed cytotoxicity. Stimulation results in activated T-lymphocytes and is dependent on the ability of the superantigen to bind to both the T cell receptor and an MHC class II antigen.

A second objective of the invention is to provide conjugates between biospecific affinity counterparts (e.g. antibodies) and superantigens with a modified affinity for MHC class II antigens. This has now been shown to improve the selectivity for superantigen antibody dependent cell cytolysis (SADCC) of cells exposing the antigen (against which the antibody/biospecific affinity counterpart of the conjugate is directed) over other cells exposing MHC class II antigens.

A third objective of the invention is to provide conjugates that can be used as the active principle in the treatment of mammals suffering from cancers, autoimmune diseases, parasitic infestations, viral infections or other diseases associated with cells that on their surface express structures that are specific for respective disease.

The Invention

The main aspect of the invention is a conjugate comprising a. a biospecific affinity counterpart that is directed towards a structure to which one intends to bind to the conjugate,
b. a peptide that
   i. is derived from a superantigen,
   ii. has the ability to bind to the Vβ chain of the T cell receptor, and
   iii. has a modified ability to bind to MHC class II antigens compared to the superantigen from which the peptide is derived (wild-type of superantigen=SA (wt)).

The peptide and the affinity counterpart are covalently linked to each other via a bridge (B).

The preferred conjugates have the ability to activate and direct T-lymphocytes to selective lysis of cells that on their surface expose the structure against which the affinity counterpart is directed. This means that the conjugates shall cause cytolysis in an SADCC mediated method (Superantigen Antibody Dependent Cellular Cytotoxicity). See the experimental part below and our previous publications concerning conjugates between superantigens and antibodies (e.g. Dohlsten et al., WO 9201470).

The inventive conjugates have a structure that is analogous to the superantigen-antibody conjugates described in the prior art (Dohlsten et al., WO 9201470 which hereby is incorporated by reference), i.e. the conjugates complies with the formula:

T—B—SA(m)

where T represents the biospecific affinity counterpart, SA(m) is the modified superantigen (the above-mentioned peptide), and B is a covalent bridge linking T and SA(m) together.

T can in principle be any structure that binds via biospecific affinity. In most important cases, T is capable of binding to a cell surface structure, preferably a disease specific structure as given above. The structure against which T is directed is usually different from (a) the Vβ chain epitope to which the superantigen derived peptide (SA(m)) binds and (b) the MHC class II antigen epitope to which the unmodified superantigen binds. The biospecific affinity counterpart T may primarily be selected among interleukins (e.g. interleukin-2), hormones, antibodies and antigen binding fragments of antibodies, growth factors etc. See for instance Woodworth, Preclinical and Clinical Development of Cytokine Toxins presented at the conference "Molecular Approaches to cancer Immunotherapy", Ashville, N.C., Nov. 7–11, 1993. Polypeptides binding to the constant domains of immunoglobulins (e.g. Proteins A and G and L), lectins, streptavidin, biotin etc were at the priority date considered to be of minor importance.

At the priority date, it was preferred that T was an antibody or an antigen binding fragment of an antibody (including Fab, F(ab)$_2$, Fv, single chain antibody etc), with particular emphasis of an antibody active fragment (such as Fab) of antibodies directed against the so called C242 epitope (Lindholm et al., WO 9301303) or against other cancer specific epitopes.

In case T is an antibody it is primarily monoclonal or a mixture of a defined number of monoclonals (e.g. 2, 3, 4, 5 or more). T may be a polyclonal antibody, in case the use is non-therapeutical.

It is not imperative for T to have a polypeptide structure. The modified superantigen SA(m) is primarily a mutated superantigen but may potentially also be a chemically modified superantigen, including fragments of superantigens retaining the ability to bind to the Vβ chain of the T cell receptor.

The expression "mutated superantigen" means that the native ability of the superantigen to bind to MHC class II antigens has been modified on the genomic level by replacing, inserting or removing one or more amino acids in the native superantigen.

Superantigen fragments obtained by mutations removing parts of the full amino acid sequence and fragments obtained by enzymatic or chemical cleavage of superantigens may be used equivalently in chemical conjugates of the invention.

The modified superantigen SA(m) may comprise one or more amino acid sequences that are derived from different superantigens and that may have been mutated, for instance combinations of the preferred superantigens mentioned below.

The modified superantigen SA(m) as such may exhibit a decreased immunogenicity and toxicity compared to the native superantigen.

Other groups/substances that are capable of cross reacting with the Vβ-chain of the T cell receptor may potentially also be employed equivalently with the mutated superantigen (SA(m)) as given above. Such groups/substances may be of non-polypeptide structure.

At the end of the priority year the most interesting product candidates of the invention comprised mutated forms of superantigens having multiple MHC class II binding sites and/or the ability to coordinate $Zn^{2+}$, for instance SEA, SED, SEE and SEH.

T as well as SA(m) may be prepared by recombinant techniques.

The bridge B may be selected as previously described (Dohlsten et al., WO 9201470), i.e. it shall preferably be hydrophilic and exhibit one or more structure(s) selected among amide, thioether, ether, disulfide etc. In case the bridge have unsubstituted unbroken hydrocarbon chains they preferably lack aromatic rings, such as phenyl. The most important bridges are those obtained by recombinant techniques, i.e. when the conjugation takes places on the genomic level. In such cases oligopeptide bridges containing hydrophilic amino acid residues, such as Gln, Ser, Gly, Glu and Arg, are preferred. Pro and His may also be included. During the priority year it has been decided that the preferred bridge is a peptide comprising three amino acid residues (GlyGlyPro).

The inventive conjugate may comprise one or more modified superantigen(s) per biospecific affinity counterpart and vice versa. This means that T in the formula above may contain one or more modified superantigens in addition to the biospecific counterpart. In analogy SA(m) may contain one or more biospecific affinity counterpart(s) T. The affinity counterpart T and SA(m) may also comprise other structures. The number of modified superantigens per affinity counterpart is preferably one or two. The synthesis of the novel inventive conjugates may be carried out in principle according to two main routes: 1. by recombinant techniques and 2. chemical linking of T to SA(m). The methods are well recognized for the ordinary skilled worker in the field and comprise a large number of variants. It follows that the invention primarily concerns artificial conjugates, i.e. conjugates that are not found in nature.

Chemical linking of a modified superantigen to the biospecific affinity counterpart T often utilizes functional groups (e.g. primary amino groups or carboxy groups) that are present at many positions in each compound. It follows that the final product will contain a mixture of conjugate molecules differing with respect to the position at which linking has taken place.

For recombinant conjugates (fusion proteins) the obtained conjugate substance will be uniform with respect to the linking position. Either the amino terminal of the modified superantigen is linked to the carboxy terminal of the biospecific affinity counterpart or vice versa. For antibodies, such as intact antibodies and antigen binding fragments (Fab, Fv etc), either the light or the heavy chain may be utilized for such fusions. At present time recombinant conjugates are preferred, with preference for Fab fragments and linking of the amino terminal of the modified superantigen to the first constant domain of the heavy antibody chain (CH1), without exclusion of the analogous linking to the light chain or to the VH and VL domain that also may give quite good results.

There are two different methods for obtaining large amounts of superantigens (including modified and fused forms) in *E. coli*: intracellular production or secretion. The latter method is preferred for the inventive conjugates because it offers purification of correctly folded protein from the periplasma and from the culture medium. Intracellular production results in a complicated purification procedure and often needs refolding in vitro of the protein (in order for the protein to obtain the correct tertiary structure). The above does not exclude that it is possible to produce active conjugates also in other host cells, e.g. eukaryotic cells, such as yeast or mammalian cells.

The production of mutated superantigens and selection of mutants having a modified ability to bind (affinity) to MHC class II antigens may be carried out according to known techniques (se e.g. Kappler et al., J. Exp. Med. 165 (1992) 387–396). See also our experimental part.

The ability of the conjugate to bind to the T cell receptor Vβ chain, to the target structure and to cause lysis of the target cell depends on i.a. the peptide (SA(m)) that is derived from a superantigen, the biospecific affinity counterpart (T) and the structure and length of the bridge (B). A person ordinary skilled in the art is able to optimize the inventive conjugates with respect to the binding ability and the ability to cause lysis by studying the relationship between effect and structure with the aid of those models that have been disclosed in connection with previously known superantigen antibody conjugates (see the above-referred publications). See also the experimental part below.

By modified ability to bind MHC class II antigens is primarily intended that the ratio $IC_{50}(SA(wt)):IC_{50}(SA(m))$ is <0.9 (90%), such as <0.5 (<50%) and possibly also <0.01 (<1%). In the alternative the modified binding ability of the inventive conjugates can be measured as the ratio of the dissociation constants $K_d(SA(wt)):K_d(SA(m))$ with $K_d$ measured in nM and with the same limits as for the ratio $IC_{50}(SA(wt)):IC_{50}(SA(m))$. For the determination of $IC_{50}$ (SA(wt), $IC_{50}(SA(m))$, $K_d(SA(m))$ and $K_d(SA(m))$ see the experimental part below.

It is previously known that certain superantigens may have two or more sites that bind to MHC class II antigen (Fraser et al., In: Superantigens: A pathogens view on the immune system. Eds. Huber & Palmer, Current Communications in Cell Molecular Biology 7 (1993) 7–29). For this type of superantigens the binding ability shall be modified at least one of the binding sites, e.g. as a reduction of the above-mentioned size. Possibly it may suffice with a superantigen modification that create a changed difference in affinity for two MHC class II binding sites, tentatively >10% and preferably by reducing the affinity of at least one site.

Superantigens bind to TCR Vβ chains of different subgroups with varying affinities. In the inventive fusion proteins/conjugates, the superantigen employed may have been modified so as to show an altered subgroup specificity or an altered affinity to one or more members of the subgroup. There are strong reasons to believe that a parabolic relationship exists between the affinity for TCR Vβ and stimulation via TCR, i.e. a moderate affinity will give the maximal stimulation. Accordingly an appropriate affinity of a modified superantigen for TCR Vβ may be at hand as soon as the fusion protein/conjugate comprising the modified superantigen is able to significantly stimulate a resting T cell population representing essentially the distribution of all human Vβ subgroups to proliferate. The T cell population may be pooled T cells from randomly selected human individuals. By significantly is meant that the stimulation is possible to measure. The results presented in Table II (right column) in the experimental part indicate that the ability to cause SADCC of the inventive conjugates/fusion proteins often is essentially the same as for the fusion comprising the wild-type superantigen.

Main Use of the Conjugates/Fusion Proteins of the Invention.

The conjugates according to the invention are primarily intended for the treatment of the same diseases as the conjugates between normal superantigens and antibodies. See the above-mentioned publications. Thus the inventive conjugates may be administered either as the main therapy or as adjuvant therapy in connection with surgery or other drugs.

The pharmaceutical composition of the invention comprises formulations that as such are known within the field but now containing our novel conjugate. Thus the compositions may be in the form of a lyophilized particulate material, a sterile or aseptically produced solution, a tablet, an ampoule etc. Vehicles such as water (preferably buffered to a physiologically pH value by for instance PBS) or other inert solid or liquid material may be present. In general terms the compositions are prepared by the conjugate being mixed with, dissolved in, bound to, or otherwise combined with one or more water-soluble or water-insoluble aqueous or non-aqueous vehicles, if necessary together with suitable additives and adjuvants. It is imperative that the vehicles and conditions shall not adversely affect the activity of the conjugate. Water as such is comprised within the expression vehicles.

Normally the conjugates will be sold and administered in predispensed dosages, each one containing an effective amount of the conjugate that, based on the result now presented, is believed to be within the range of 10 μg–50 mg. The exact dosage varies from case to case and depends on the patient's weight and age, administration route, type of disease, antibody, superantigen, linkage (—B—) et.

The administration routes are those commonly known within the field, i.e. a target cell lysing effective amount or a therapeutically effective amount of a conjugate according to the invention is contacted with the target cells. For the indications specified above this mostly means parenteral administration, such as injection or infusion (subcutaneously, intravenously, intra-arterial, intramuscularly) to a mammal, such as a human being. The conjugate may be administered locally or systemically.

By "target cell lysing effective amount" is contemplated that the amount is effective in activating and directing T-lymphocytes to destroy the target cell.

At the end of the priority year it had been decided that the preferred administration route for conjugates/fusion proteins comprising unmodified superantigens is 3 hours' intravenous infusion per day combined with a fever-reducing agent (paracetamol). The administration is to be repeated during 4 days and stopped before dsecondary antibodies are raised against the fusion protein/conjugate in the patient. This dosage schedule is likely to be applicabple also to the present inventive conjugates/fusion proteins.

Alternative Fields of Use.

The inventive conjugates can also be employed to quantitatively or qualitatively detect the structure against which the target-seeking group (T) is directed. In general these methods are well-known to people in the field. Thus, the modified superantigen may function as a marker group within immunoassays including immunohistochemistry meaning that the marker group in turn is detected by for instance an antibody that is directed towards the peptide (SA(m)) and labelled with an enzyme, isotope, fluorophor or some other marker group known per se. Another immunoassay method is to detect in a cell population cells that on their surface express a structure capable of binding to the target-seeking group (T). This use means that a sample from the cell population is incubated with T-lymphocytes together with the present inventive conjugate as in an SADCC assay. In case the incubation leads to cell lysis this is an indication that the population contains cells that on their surface express the structure.

Experimental Part

Manufacture of Recombinant Proteins

Antibodies

The experimental work in connection with the invention has primarily been done with monoclonal antibody C215 as a model substance. This antibody is directed against an antigen in the GA-733 family (see for instance EP 376,746) and references cited therein and Larsson et al., Int. J. Canc. 32 (1988) 877–82). The C215 epitope has been judged not to be sufficiently specific fox cancer treatment in humans. At the priority date mab C242 (Lindholm et al., WO 9301303) was believed to be a better candidate, as judged from experiments with its fusion product with wild-type SEA.

Bacterial Strains and Plasmids

The E. coli strains UL635 (xyl-7, ara-14, T4$^R$, $\Delta$ompT) and HB101 (Boyer and Roulland-Dessoix, J. Mol. Biol. 41 (1969) 459–472) were used for the expression and cloning, respectively. The vector pKP889 was used for expression of Fab-SEA fusion proteins (derived from the murine antibody C215) and the vectors pKP943 and pKP1055 for secretion of SEA (FIG. 1). The Fab-SEA expression vector pKP889 is identical to pKP865 (Dohlsten et al, Proc. Natl. Acad. Sci. USA (1994) in press) except that the spacer between $C_H1$ and SEA is GlyGlyAlaAlaHisTyrGly SEQ. ID. NO. 1. Expression from pKP943 yields SEA with the native amino terminus. The use of pKP1055 results in SEA having a Gly residue added at the amino terminus. In both vectors the signals from staphylococcal protein A (Uhlén et al., J. Biol. Chem. 259 (1984) 1695–1702) are used for transcription and translation and a synthetic signal peptide for secretion (L. Abrahmsén, unpublished).

In Vitro Mutagenesis

Mutations were made by polymerase chain reactions run on a Perkin Elmer Thermocycler. The reaction mixture (100 µl) contained: 1×PCR buffer from Perkin Elmer Cetus (10 mM Tris/HCl pH 8.3, 1.5 mM $MgCl_2$, 0.001% (w/v) gelatine, an additional 2 mM $MgCl_2$, 0.4 mM dNTPs (Perkin Elmer Cetus), 2.5 units of Ampli Taq DNA polymerase (Perkin Elmer Cetus, USA) and 100 ng DNA template. Primers were added to a final concentration of 0.8 µM. The original template was a plasmid containing *Staphylococcus aureus* enterotoxin A gene identical to the one published by Betley et al. (J. Bacteriol. 170 (1988) 34–41), except that the first codon (encoding Ser) was changed to TCC to furnish a Bam HI site at the 5' end of the gene. Later a derivative containing more unique restriction enzyme sites introduced by silent mutations was used. Mutations introduced next to a restriction site were made with one set of primers, one of these spanning the mutation and the restriction site. For most mutations two set of primers had to be used and the PCR was performed in two consecutive steps. A new restriction enzyme site was introduced together with each mutation to enable facile identification. Oligonucleotides used as primers were synthesized on a Gene Assembler (Pharmacia Biotech AB, Sweden). To confirm each mutation the relevant portion of the nucleotide sequence was determined on an Applied Biosystems DNA-Sequenser using their Taq DyeDeoxy Termination Cycle Sequencing Kit.

Protein Production and Analysis

E. coli cells haboring the different gene constructs were grown overnight at room temperature (Fab-SEA vectors) and at 24–34° C. (secretion vectors, the optimum depends on the mutation). The broth was 2×YT (16 g/l Bacto trypton, 10 g/l Bacto yeast extract, 5 g/l NaCl) supplemented with kanamycin (50 mg/l). Fusion proteins were induced by addition of isopropyl-$\beta$-D-thiogalactoside to a final concentration of 100 µM. (The protein A promotor used in the expression of non-fused SEA is constitutive). The cells were pelleted at 5000×g and the periplasmic contents were released by gently thawing the previously frozen cell pellet in 10 mM Tris-HCl (pH 7.5) on ice during agitation for 1 hour. The periplasmic extracts were clarified by centrifugation at 9500×g for 15 minutes. The Fab-SEA proteins were used without further purification. SEA and Gly-SEA were further purified by affinity chromatography on an anti-SEA antibody column. Polyclonal rabbit anti-SEA antibodies were previously collected from rabbits preimmunized with SEA and purified by affinity chromatography on protein G Sepharose® (Pharmacia Biotech).

Protein Analysis

The proteins were separated in precast polyacrylamide SDS Tris-Glycine Novex gels (gradient 4–20% or homogenous 12%, Novex novel experimental technology) and either stained with Coomassie Blue or used in Western blot. Polyclonal rabbit anti-SEA antibodies (above) were used to detect SEA in Western blot analysis, followed by porcine anti-rabbit Ig antibodies, and rabbit anti-horseradish peroxidase antibodies and peroxidase. With Fab-SEA fusion proteins peroxidase conjugated rat antibodies recognizing the kappa chain were also used (AAC 08P, Serotech LTD, England). 3,3'-diaminobenzidine (Sigma) was used for visualization of peroxidase.

Circular dichroism (CD) spectra were collected in a J-720 spectropolarimeter (JASCO, Japan) at room temperature (22–25° C.) in 10 mM phosphate buffer, pH 8.2, with 0.02 mM $ZnSO_4$ and 0.005% (v/v)$^-$ Tween® 20. The scanning speed was 10 nm/min and each spectrum was averaged from five subsequent scans. The cell path length was 1 mm and the protein concentration 0.2 to 0.5 mg/ml. Guanidine hydrochloride (Gdn-HCl) denaturations at equilibrium were measured at 23° C. by CD at 222 nm with a protein concentration of 0.3 mg/ml and a cell path length of 1 mm. These data were used to calculate the apparent fraction of unfolded protein ($F_{app}$). Equilibrium unfolding parameters were derived by fitting the data to a two-site folding process (Hurle et al., Biochemistry 29 (1990) 4410–4419.

Binding and Functional Assays In Vitro

Materials

Reagents: RPMI 1640 medium obtained from Gibco, Middlesex, England was used. The medium had a pH of 7.4 and contained 2 mM L-glutamine (Gibco, Middlesex, England), 0.01 M HEPES (Biological Industries, Israel), 1 mM $NaHCO_3$ (Biochrom AG, Germany), 0.1 mg/ml Gentamycin sulphate (Biological Industries, Israel), 1 mM Na-pyruvate (JRH Biosciences Industries, USA), 0.05 mM mercaptoethanol (Sigma Co., USA), 100 times concentrated non-essential amino acids (Flow Laboratories, Scotland) and was supplemented with 10% fetal bovine serum (Gibco, Middesex, England). Recombinant SEA(wt), SEA(m) and the fusion products C215Fab-SEA(wt) and C215Fab-SEA (m) were obtained as described above. Human recombinant IL-2 was from Cetus Corp., USA. Mitomycin C was from Sigma Co., USA. $Na_2^{51}CrO_4$ was obtained from Merck, Germany. Phosphate buffered saline (PBS) without magnesium and calcium was received from Imperial, England.

Cells: The human colon carcinoma cell line Colo205 and the B cell lymphoma cell line Raji were obtained from American Type Cell Culture Collection (Rockville, Md., USA) (expressing HLA-DR3/w10, -DP7, -DQw1/w2). The EBV-transformed lymphoblastoid B cell line BSM was a generous gift from Dr van De Griend, Dept of Immunology, Dr Daniel den Hoed Cancer Center, Leiden, the Netherlands. The cells were repeatedly tested for mycoplasma contamination with Gen-Probe *Mycoplasma* T.C. test, Gen-Probe Inc., San Diego, USA.

SEA activated T cell lines were produced by activation of mononuclear cells from peripheral blood. The blood was received as buffy coats from blood donors at the University Hospital of Lund. The PBMs were stimulated at a concentration of $2 \times 10^6$ cells/ml with mitomycin C treated SEA coated BSM cells (preincubated with 100 ng/ml SEA) in medium with 10% FCS. The T cell lines were restimulated biweekly with 20 U/ml human recombinant IL-2 and weekly with mitomycin C treated SEA coated BSM cells. The cell lines were cultivated for 4–12 weeks before being used in the assay.

The viability of the effector cells, as determined by trypan blue exclusion, exceeded 50%.

Determination of MEC Class II Binding Characteristics of Wild-Type and Mutant SEA Radioiodination procedure. Appropriate amounts of wild-type or mutant SEA were radiolabeled with 10 to 25 mCi $Na^{125}I$ using enzymobeads with the lactoperoxidase technique (NEN, Boston, Mass.). The reaction was stopped by quenching with sodium azide and protein-bound radioactivity was separated from free iodine by filtration through a PD-10 column (Pharmacia Biotech AB, Sweden) with R10 medium as elution buffer. Conditions were chosen to obtain a stoichiometric ratio between iodine-125 and protein of $\leq 2:1$. The radiochemical purity was verified by size-exclusion chromatography on a TSK SW 3000 HPLC column. The effect of the radioiodination on the binding activity was only tested for wild-type SEA and found not to be affected (data not shown).

Direct binding assay. Raji cells, $6 \times 10^4/100$ μl, previously cultivated in R10 medium, were added to conical polypropylene tubes and incubated (22° C./45 min) in triplicate with 100 μl/tube of serially diluted $^{125}I$-labeled wild-type or mutant SEA. The cells were washed with 2 ml 1% (w/v) bovine serum albumin (BSA) in 10 mM phosphate-buffered saline (PBS), pH 7.4, centrifugated at 300×g for 5 minutes and aspirated. This procedure was repeated twice. Finally, the cells were analyzed for cell-bound radioactivity in a gamma counter (Packard Instruments Co, Downers Grove, Ill., USA). The apparent dissociation constant, $K_d$, and the number of binding sites, N, at saturation were calculated according to Scatchard (Ann. N.Y. Acad. Sci. 51 (1949) 660–72) after subtraction of non-specific binding (i.e. binding after incubation with R10 medium alone.

Inhibition assay (inhibition of $^{125}I$-labeled wild-type SEA binding by mutant SEAs). These inhibition experiments were carried out as is described for the direct binding assay with slight modifications. Briefly, 50 μl of $^{125}I$-labeled wild-type SEA was allowed to compete with an excess of unlabeled wild-type or mutant SEA (50 μl/tube) for binding to $6 \times 10^4/100$ μl Raji cells. A tracer concentration yielding≈40% bound radioactivity in the direct assay was used to obtain maximal sensitivity in the inhibition assay. The displacement capacity of the competitor was expressed as the concentration yielding 50% inhibition ($IC_{50}$) of bound radioactivity. The binding affinity of the mutants relative to wild-type SEA was calculated using the equation:

$$IC_{50}(SEA(wt)):IC_{50}(SEA(m))$$

In order to analyze whether the mutants compete for binding to the same site on Raji cells as wild-type SEA, the binding data obtained with SEA mutants were plotted as a log-logit function and tested for parallelism with the corresponding data for wild-type SEA.

Inhibition assay (inhibition of the binding of fluorescent-labeled wild-type SEA by unlabeled wild-type SEA and SEA mutants). Raji cells ($2.5 \times 10^5$) were incubated with inhibitor (wild-type or mutant SEA; 0–6000 nM) diluted in 50 μl $CO_2$-independent medium (Gibco) supplemented with 10% FCS, glutamine and gentamycin at 37° C. for 30 minutes. Fluorescein conjugated wild-type SEA was added to a final concentration of 30 nM and the samples were incubated for an additional half hour at 37° C. The samples were washed three times with ice cold PBS supplemented with 1% BSA (PBS-BSA) and finally kept in 0.4 ml PBS-BSA on ice until they were analyzed. From each sample 10 000 live cells were analyzed for green fluorescence on a FACStar® (Becton Dickinson) flow cytometer and the mean fluorescence value was calculated using the LYSIS II program.

SDCC and SADCC Assays of SEA(wt), SEA(m) and their Fusion Proteins with C215Fab.

SDCC-assays. The cytotoxicity of SEA(wt), SEA(m) and their fusions with C215Fab against MHC class II⁺ Raji cells was analyzed in a standard 4 hour $^{51}Cr^{3+}$-release assay, using in vitro stimulated SEA specific T cell lines as effector cells. Briefly, $^{51}Cr$ labeled Raji cells were incubated at $2.5 \times 10^3$ cells per 0.2 ml medium (RPMI, 10% FCS) in microtitre wells at defined effector to target cell ratio in the presence or absence (control) of the additives. Percent specific cytotoxicity was calculated as 100×([cpm experimental release–cpm background release]/[cpm total release–cpm background release]). The effector to target cell ratio was 30:1 for unfused SEAs and 40:1 for fusion proteins.

SADCC against of human colon cancer cells. The cytotoxicity of C215Fab-SEA(wt), C215Fab-SEA(m), SEA(wt) and SEA mutants against C215⁺ MHC class II⁻ colon carcinoma cells SW 620 was analyzed in a standard 4 hour $^{51}Cr^{3+}$-release assay, using in vitro stimulated SEA specific T cell lines as effector cells. Briefly, $^{51}Cr^{3+}$-labeled SW 620 cells were incubated at $2.5 \times 10^3$ cells per 0.2 ml medium (RPMI, 10% FCS) in microtitre wells at effector to target cell ratio 30:1 in the presence or absence (control) of the additives. Percent specific cytotoxicity was calculated as for SDCC assays.

In Vivo Functional Experiments

Tumor cells. B16–F10 melanoma cells transfected with a cDNA encoding the human tumor associated antigen C215 (B16–C215) (Dohlsten et al., Monoclonal antibody-superantigen fusion proteins: Tumor specific agents for T cell based tumor therapy; Proc. Natl. Acad. Sci. USA, In press, 1994), were grown as adherent cells to subconfluency. The culture medium consisted of RPMI 1640 (GIBCO, Middlesex, UK) supplemented with $5 \times 10^{-5}$ β-mercaptoethanol (Sigma, St Louis, Mo., USA), 2 mM L-glutamine (GIBCO), 0.01 M Hepes (Biological Industries, Israel) and 10% fetal calf serum (GIBCO). The cells were detached by a brief incubation in 0.02% EDTA and suspended in ice cold phosphate buffered saline with 1% syngeneic mouse serum (vehicle) to $4 \times 10^5$ cells/ml.

Figure 5:
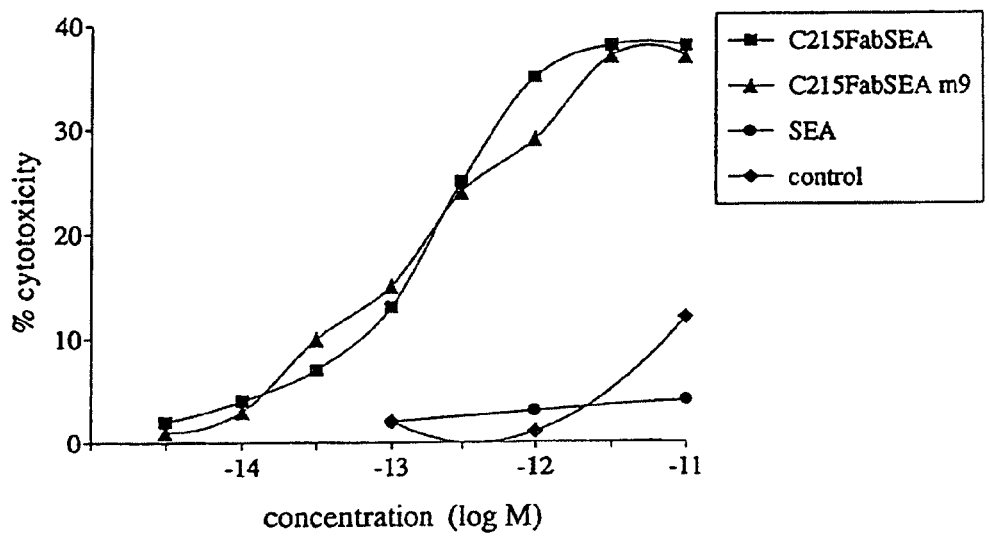

Animals and animal treatment. The mice were 12–19 weeks old C57B1/6 mice transgeneic for a T cell receptor Vβ3 chain (Dohlsten et al., Immunology 79 (1993) 520–527). One hundred thousand B16–C215 tumor cells were injected i.v. in the tail vein in 0.2 ml vehicle. On day 1, 2 and 3, the mice were given i.v. injections of C215Fab-SEA(wt) or C215Fab-SEA(D227A) in 0.2 ml vehicle at doses indicated in the FIGS. 5a and 5b. Control mice were given only vehicle according to the same schedule. On day 21 after tumor cell injection, the mice were killed by cervical dislocation, the lungs removed, fixed in Bouin's solution and the number of lung metastases counted.

Results

"Alanine Scanning" of Staphylococcal Enterotoxin A.

Initially the structure of SEA was unknown and only speculations could be done about what side chains were surface accessible. Therefore, the majority of the mutants were chosen from alignments of homologous superantigens (Marrack and Kappler, Science 248 (1990) 705–711). Conserved (mainly polar) residues were chosen on the rational that some of these superantigens are expected to bind to HLA-DR in a conserved fashion (Chitagumpalak et al., J. Immunol. 147 (1991) 3876–3881). Alanine replacements were used according to published strategies (Cunnningham and Wells, Science 244 (1988) 1081–1085). During the course of this work the available information increased: i) it was shown that a $Zn^{2+}$ ion is important for the interaction between SEA and MHC class II (HLA-DR) (Fraser et al., Proc. Natl. Acad. Sci. USA 89 (1991) 5507–5511), ii) a mutational analysis of staphylococcal enterotoxin B (SEB) was presented (Kappler et al., J. Exp. Med. 175 (1992) 387–396), and iii) the structure of SEB was presented (Swaminathan et al., Nature 359 (1992) 801–806).

Our first mutant showing a severely reduced affinity for HLA-DR, D227A, was found to co-ordinate the $Zn^{2+}$ ion very poorly (data not shown). Assuming a common fold for SEA and SEB, the new data suggested two MHC class II binding regions; one involving the $Zn^{2+}$ ion and one corresponding to the site defined in SEB. A second set of mutations were made on these assumptions. This second set of mutants were expressed in the form of SEA carrying a glycine added at the amino terminus. First the extension was shown to have no effects on the binding properties of wild-type SEA (next section).

Most of the mutants were expressed and secreted by *E. coli* in a functional form as judged by analysis of the binding of monoclonal antibodies (Table I). Very low amounts were obtained of the mutants E154A/D156A and R160A. Consequently these were excluded from the study. The mutants having an Ala substitution in residues 128, 187, 225 or 227 were not recognized by the monoclonal antibody 1E. The latter two mutants showed a reduced level of expression (more pronounced at 34° C. than at 24° C.) and migrated faster during SDS-PAGE, under denaturing but not reducing conditions (all other mutants migrated as wild-type SEA, data not shown). As judged by CD spectra analysis the structure of D227A could differ slightly from native SEA (FIG. 2), but the stability was very close to wild-type SEA (measured as resistance towards guanidine hydrochloride denaturation). The calculated ΔΔG between the mutant and native SEA (SEA(wt)) was −0.16 kcal/mol and is only about 4% of the ΔG° values (data not shown). Overall the signals in the CD analysis were low, as expected from a mostly β-sheet structure. It was recently reported that His 225 co-ordinates $Zn^{2+}$ (unpublished data in Fraser et al (Proc. Natl. Acad. Sci. USA 89 (1991) 5507–5511). Since Asp 227 is involved in $Zn^{2+}$ co-ordination (above) and presumably located in the same β-sheet as His 225 this suggests that these two residues constitutes the zinc-binding nucleus found in zinc-co-ordinating proteins (Vallee and Auld, Biochemistry 29 (1990) 5647–5659).

Binding to MHC Class II and T Cell Receptor

The MHC class II affinity was calculated from the amounts needed to compete with fluorescein-labeled wild-type SEA for Raji cell exposing large amounts of MHC class II. The displacement capacity of a mutant was calculated from the concentration yielding 50% inhibition ($IC_{50}$) of bound fluorescence compared with the concentration needed with wild-type SEA as the competitor. For wild-type SEA and for some mutants, the result from this analysis was compared with the result from an analysis where $^{125}I$ labeled wild-type SEA was used as the tracer. As may be seen in Table II, the values obtained from these two inhibition analyses correlate well.

For six selected mutants the binding to MHC class II was measured directly using $^{125}I$ labeled mutant SEA (Table II). With the mutant H50A the values obtained from the direct binding assay and the inhibition assays correlated well but with the mutant F47A a large discrepancy was found: the direct binding indicated only 7 times weaker binding than wild-type SEA but both competition analyses demonstrated around 70 times reduced binding. The data from two of the other mutants indicated two separate binding interactions. For the mutants H225A and D227A the affinity was below the detection limit also in this analysis.

We previously showed that fusion proteins composed of the Fab fragment of a carcinoma reactive antibody and SEA could be used to direct cytotoxic T cells to specifically lyse cancer cells, while the interaction between SEA and the T cell receptor (TCR) was too weak to be detected by itself (Dohlsten et al., Proc. Natl. Acad. Sci. USA, in press). Thus, in contrast to analyses involving the isolated superantigen the Fab fusion context enables a functional assay for the interaction between SEA and the TCR, independent of the MHC class II binding. Consequently, the efficiency of the different conjugates to direct T cells to lyse cells recognized by the Fab moiety was monitored in a chromium release assay. This analysis confirmed that the mutations shown to affect the MHC class II binding did not affect the TCR binding (Table II).

Biological Effects of the Mutations

The proliferative effect was measured as the ability to stimulate-peripheral lymphocytes to divide. All three mutants that competes very poorly for MHC class II induced little or no proliferation and the intermediate mutant H187A displayed some proliferative capacity, whereas the other investigated mutants were indistinguishable from the wild-type (table III). Harris et al (Infect. Immun. 61 (1993) 3175–3183) recently reported a similar severe reduction in T cell stimulatory activity for the SEA mutants F47G and L48G. Clearly a strong reduction in any of the two suggested binding regions results in a severe effect on the ability to induce proliferation. This suggests that SEA cross-links two molecules of MHC class II leading to dimerization of the TCR and that this is needed to yield a signal transduction.

In contrast the efficiency of the different mutants in directing in vitro stimulated SEA T cells to lyse MHC class II bearing target cells shows correlation with the binding affinity, rather than to the ability to compete (Table III). For example, the efficiency of F47A and D227A are only reduced 2.5 times and 300 times, respectively. Thus, here no inherent requirement for divalency too is obvious. The increase in multivalency resulting from the significantly larger number of TCRs on the surface of activated T cells might partially shield the effect of a lower avidity in the SEA/MHC class II interaction. That dimerization is not needed to direct T cell cytotoxicity has previously been demonstrated by the use of carcinoma specific bifunctional antibodies containing one anti-CD3 moiety and one anti-carcinoma moiety (Renner et al., Science 264 (1994) 833–35).

Figure 6A:
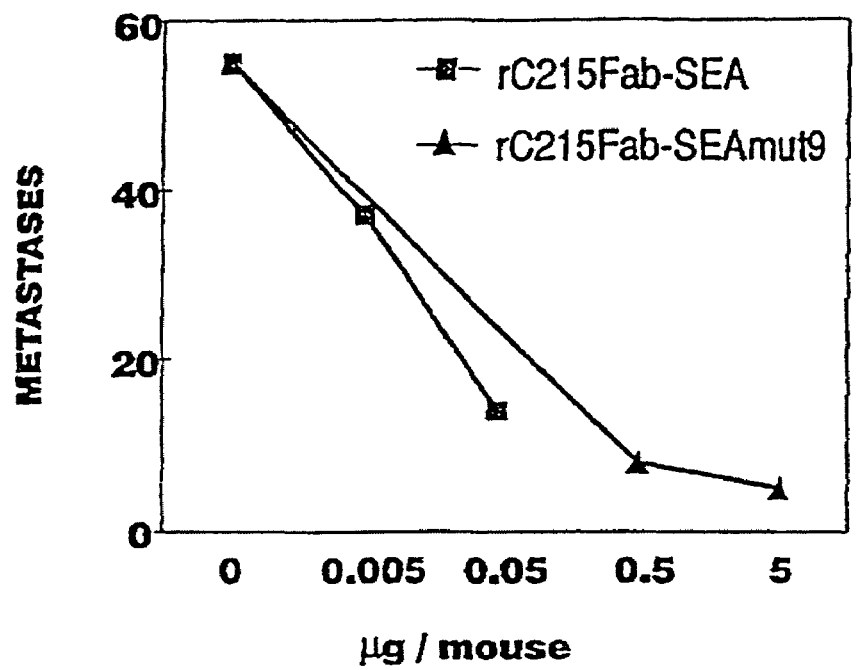
Figure 6B:
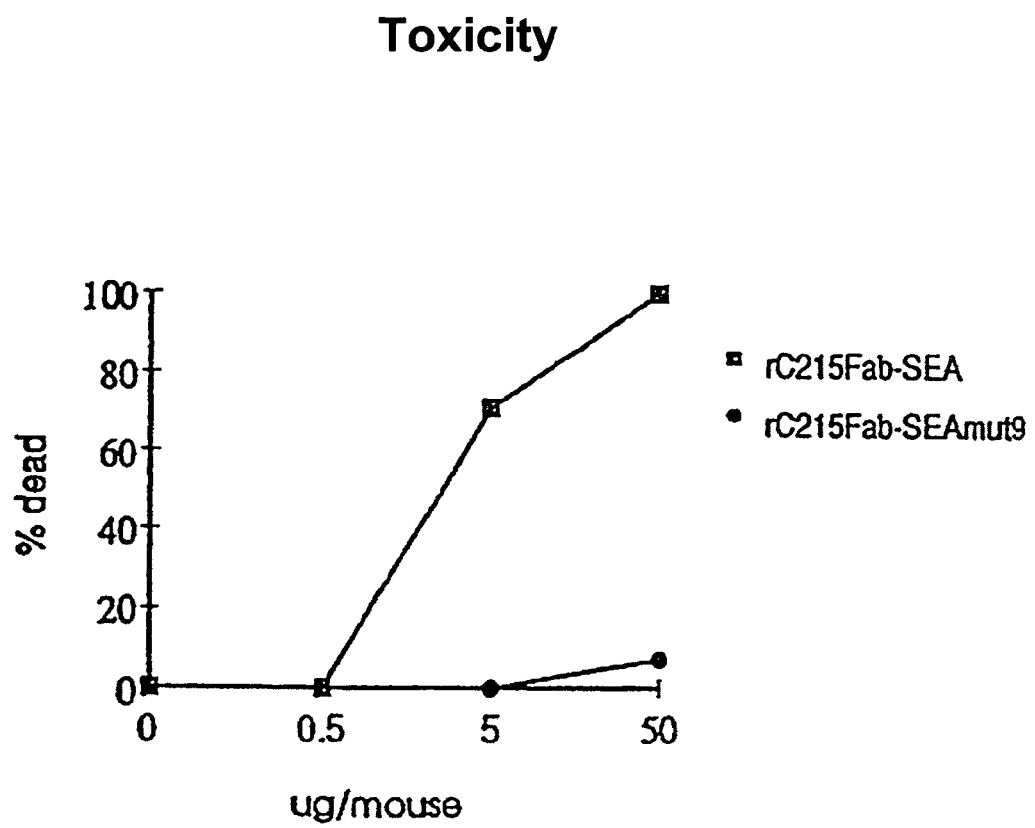

In vivo functional experiments: The results are represented in FIGS. 6a and 6b. Treatment of mice with C215Fab-SEA(wt) and C215Fab-SEA(D227A) were both highly effective in reducing the number of lung metastases of B16–C215 melanoma cells. The therapeutic effect was essentially identical for the two variants of the targeted superantigens. Treatment with C215Fab-SEA(wt) resulted in 70% lethality at doses of 5 μg/injection. In contrast, no mice died when the same dose of C215Fab-SEA(D227A) were used. Taken together, SEA(D227A) is an example of a mutant with reduced toxicity and retained therapeutic efficiency when incorporated in a Fab-SEA fusion protein.

Discussion

The structure of the complex between SEB and HLA-DR was recently reported (Jardetzky et al., Nature 368 (1994) 711–718). Most of the SEB residues identified to be involved in this interaction are conserved in SEA. Our data on mutant D227A indicates a weak affinity for the interaction between this site of SEA (the amino proximal site) and the MHC class II, having a $K_d$ value higher than 8 μM. The $K_d$ for the interaction between SEB and HLA-DR was recently reported to be 1.7 μM (Seth et al., Nature 369 (1994) 324–27). The different interactions between SEB, TCR and HLA-DR were investigated and it was shown that the complex between SEB and HLA-DR was not stably maintained in the absence of TCR. Plasmon resonance experiments indicated that this was because of a very fast off-rate. The avidity effects obtained if SEA cross-links two molecules of MHC class II followed by a subsequent dimerization of the TCR could explain how SEA may induce proliferative effects at concentrations well below the $K_d$. Assuming that the mutation F47A reduces the affinity of the amino proximal site below significance, the $K_d$ of the $Zn^{2+}$ site is around 95 nM. This hypothesis was recently strengthened by the observation that the mutants F47R, F47R/H50A and F47R/L48A/H50D show identical affinity for MHC class II as F47A (unpublished).

Based on the SEB structure (Kappler et al., J. Exp. Med. 175 (1992) 387–396) and on homology alignments (Marrack and Kappler, Science 248 (1990) 705–711), it is strongly suggested that His225 and Asp227 are located in the same β-sheet and thus the side chains could be proximal. Thus, most likely these two residues constitute the zinc-binding nucleus found in zinc-co-ordinating proteins (Vallee and Auld, Biochemistry 29 (1990) 5647–5659). Similarly to these mutants, the mutants with a replacement at residue 128 or 187 are also recognized by all monoclonals except 1E. Fraser et al (Proc. Natl. Acad. Sci. USA 89 (1991) 5507–5511) showed that $Zn^{2+}$ is bound to SEA and is needed for a high affinity interaction with MHC class II. The affinity for zinc was not affected by the addition of HLA-DR. Based on this observation and the high affinity for $Zn^{2+}$ ($K_d$ of around 1 μM) a co-ordination exclusively provided by SEA and involving 4 fold co-ordination was suggested. Our data indicates an involvement of the four residues N128, H187, H225 and D227. The function of the former two residues is not yet clear; instead of providing a is ligand N128 could help in the deprotonation of D227. One argument for this is that the effect of replacing D227 is more severe that when replacing H225.

It was previously reported that there is a lack of correlation between the affinity of different superantigens for the MHC class II and the capacity to stimulate T cells to proliferate (Chintagumpala et al., J. Immunol. 147 (1991) 3876–3881). These results might partly be explained by different affinities of the superantigens towards different TCR Vβ-chains. Here we have observed the same lack of correlation but in contrast to separate superantigens the mutants display identical TCR affinity as shown in the Fab-SEA context (measured as SADCC). The most likely explanation for the lack of correlation is that two binding regions identified in this analysis represent two separate binding sites that yields not only a co-operative binding, but which results in the cross-linking of two molecules of MHC class II, which in turn yields dimerization of two molecules of the T cell receptor. This would imply that the affinity of both sites are important to obtain the proliferative effect. A high avidity results from the interactions within a hexameric complex involving two molecules of SEA, TCR and MHC class II. Thus the strong affinity/avidity of SEA towards MHC class II enables SEA interaction with the TCR despite a low direct affinity.

Other biospecific affinity counterparts: A fusion protein of SEA(D227A) and an IgG-binding domain of staphylococcal protein A has been produced by recombinant technology and expressed in E. coli. This reagent has successfully been used to target T-lymphocytes to Mot 4 and CCRF-CEM cells (obtained from ATCC) that are CD7 and CD38 positive but HLA-DP, -DQ and -DR negative. The Mot 4 and CCRF-CEM cells were preincubated with anti-CD7 or anti-CD38 mouse monoclonals (Dianova, Hamburg, Germany). In order to enhance binding between the mouse monoclonals and the IgG-binding part of the fusion protein rabbit anti-mouse Ig antibody was also added.

In comparison with protein A-SEA(wt), protein A-SEA (D227A) had a deccreased ability to bind to Daudi cells expressing MHC class II antigen.

TABLE I

Confirmation of mutant structural integrity. The binding of six monoclonal antibodies was monitored.

| Mutation | Monoclonal antibody | | | | | |
|---|---|---|---|---|---|---|
| | 1A | 2A | 3A | 1E | 4E | EC-A1 |
| Wild-type | + | + | + | + | + | + |
| D11A/K14A | + | + | + | + | + | + |
| D45A | + | + | + | + | + | + |
| F47A | + | + | + | + | + | + |
| H50A | (+) | + | (+) | + | + | + |
| K55A | + | + | + | + | + | + |
| H114A | + | + | + | + | + | + |
| K123A/D132G | + | + | + | + | + | + |
| N128A | + | + | + | − | + | + |
| K147A/K148A | + | + | + | + | − | + |
| E154A/D156A | ND | ND | ND | + | ND | ND |
| R160A | ND | ND | ND | + | ND | ND |
| H187A | + | + | + | − | + | + |
| E191A/N195A | + | + | + | + | + | + |
| D197A | + | + | + | + | + | + |

TABLE I-continued

Confirmation of mutant structural integrity. The binding of six monoclonal antibodies was monitored.

| Mutation | Monoclonal antibody | | | | | |
|---|---|---|---|---|---|---|
| | 1A | 2A | 3A | 1E | 4E | EC-A1 |
| H225A | − | + | + | − | + | + |
| D227A | + | + | + | − | + | + |

Footnotes: A plus sign indicates binding, parenthesis indicate 50 to 90% binding compared with wild-type SEA. ND means not determined.

TABLE II

Binding of SEA mutants to the MHC class II and the T cell receptor. The latter was monitored as the ability to direct activated cytotoxic T-cells specifically to lyse carcinoma cells using Fab-SEA fusions of the different mutants (SADCC).

| Mutation | $IC_{50}$ (nM) SEA-FITC[1] | $IC_{50}$ (nM) $^{125}$I-SEA[1] | $K_d$ (nM) $^{125}$I labeled[1] | SADCC (% of wild-type[1] |
|---|---|---|---|---|
| wild-type | 50 | 38 | 13 | 100[2] |
| Gly-SEA | 50 | ND | ND | 100[2] |
| D11A/K14A | 50 | ND | ND | ND |
| D45A | 53 | ND | ND | ND |
| F47A | 3150 | 2943 | 95 | 100 |
| H50A | 150 | 132 | 32 | 100 |
| K55A | 44 | ND | ND | ND |
| H114A | 48 | ND | ND | ND |
| K123A/D132G | 188 | 75 | 12/237 | 100 |
| N128A | 1150 | ND | 2.9/76 | 100 |
| K147A/K148A | 58 | ND | ND | ND |
| H187A | 1030 | 602 | 97 | 100 |
| E191A/N195A | 51 | ND | ND | ND |
| D197A | 78 | ND | ND | ND |
| H225A | >9000 | 9600 | ND | ND |
| D227A | >9000 | >10000 | >8000 | 100 |

Footnotes:
[1]ND means not determined.
[2]In the Fab-SEA context the spacer between $C_H1$ and SEA ends with a Gly.

TABLE III

Biological effects of the mutations. The ability to stimulate resting T cells to proliferate and the ability to direct cytotoxic cells to lyse MHC class II exposing target cells were monitored (SDCC = Superantigen Dependent mediated Cellular Cytotoxicity).

| Mutation | Proliferation % | SDCC $EC_{50}$ (relative) |
|---|---|---|
| wild-type | 100 | 1 |
| Gly-SEA | ND | 1 |
| D11A/K14A | ND | 0.8 |
| D45A | 50 | 1.3 |
| F47A | <0.2 | 2.5 |
| H50A | 20 | 1.4 |
| K55A | 100 | 1.3 |
| H114A | ND | 1 |
| K123A/D132G | 40 | 2.1 |
| N128A | 40 | 1.2 |
| K147A/K148A | ND | 0.7 |
| E154A/D156A | ND | ND |
| R160A | ND | ND |
| H187A | 15 | 4 |
| E191A/N195A | 100 | 1.1 |
| D197A | ND | 1.3 |

TABLE III-continued

Biological effects of the mutations. The ability to stimulate resting T cells to proliferate and the ability to direct cytotoxic cells to lyse MHC class II exposing target cells were monitored (SDCC = Superantigen Dependent mediated Cellular Cytotoxicity).

| Mutation | Proliferation % | SDCC $EC_{50}$ (relative) |
|---|---|---|
| H225A | <0.2 | $3 \times 10^2$ |
| D227A | <0.01 | $3 \times 10^2$ |

Footnotes: ND means not determined.

BRIEF DESCRIPTION OF THE DRAWINGS

General: The mutant SEA(D227A) (=SEA(m9) or mutant m9) was at the priority date the most promising SEA variant. We have therefore selected to present in vitro and in vivo results with this variant (FIGS. 3–6).

FIG. 1.

Schematic outline of the plasmids used to express SEA and C215Fab-SEA. The coding regions and the two transcription terminators following the product genes are indicated by boxes. The gene encoding the kanamycin resistance protein is labeled Km. lacI is the lac repressor gene. $V_H$ and $C_H1$ indicates the gene encoding the $F_d$ fragment of the heavy chain of the murine antibody C215. Likewise $V_K$ and $C_K$ indicates the gene encoding the kappa chain. Rop is the gene encoding the replication control protein from pBR322. The promoters directing transcription of product genes are shown as arrows, in pKP889 the trc promotor and in the other two vectors the promotor from staphylococcal protein A (spa). The region containing the origin of replication is indicated by ori. The only difference between SEA encoded by pKP943 and pKP1055 is a glycine residue added at the N-terminus of the latter. The SEA gene contained in the latter vector also contains more unique restriction enzyme sites, introduced by silent mutations.

FIG. 2

Circular dichroism spectra for wild-type SEA and for the mutants F47A and D227A, representing the most severely reduced mutations in each MHC class II binding region. The solid line is the curve for wild-type SEA. The curves for the mutants are dotted or center, F47A respectively D227A.

FIG. 3 shows the concentration dependency of superantigen dependent mediated cellular cytotoxicity (SDCC) for SEA(wt) and SEA(D227A).

FIG. 4 shows the concentration dependency of superantigen dependent cell mediated cytotoxicity (SDCC) for C215Fab-SEA(wt) and C215Fab-SEA(D227A).

FIG. 5 shows the concentration dependency of superantigen mAb dependent cell mediated cytotoxicity (SADCC) for C215Fab-SEA(wt) and C215Fab-SEA(D227A) compared to free SEA(wt).

FIG. 6*a* compares the therapeutic effects obtained in C57B1/6 mice carrying lung metastases of B16–C215 melanoma cells by treatment with C215Fab-SEA(wt) and C215Fab-SEA(D227A).

FIG. 6*b* shows toxicity of C215-SEA(wt) and C215-SEA (D227A) for the treatments represented in FIG. 6*a*.

What is claimed is:

1. A method for the treatment of a disease condition in a mammal, which condition means the presence of specific cells that are associated with the condition by the expression of a disease specific cell surface structure, wherein one administers to the mammal a therapeutically effective amount of covalent conjugate that is able to activate T lymphocytes to lyse cells that carry the disease specific cell surface structure and comprises:
   a. a biospecific affinity counterpart that is capable of binding to said surface structure, and
   b. a peptide that
      i. contains an amino acid sequence that is derived from staphylococcal enterotoxin A, wherein said peptide has the ability to bind to a Vβ of a T cell receptor, and
      ii. has been mutated in that amino acid substitution D227A has been made in staphylococcal enterotoxin A to show a modified ability to bind to MHC class II antigens.

2. A method for the treatment of a disease condition in a mammal, which condition is associated with cells having a disease specific cell surface structure comprising the step of administering a therapeutically effective amount of a covalent conjugate comprising:
   a. a biospecific affinity counterpart that is capable of binding to said surface structure, and
   b. a peptide that
      i. contains an amino acid sequence that is derived from staphylococcal enterotoxin A, wherein said peptide has the ability to bind to a Vβ of a T cell receptor, and
      ii. has been mutated in that the following amino acid residue has been substituted D227A in staphylococcal enterotoxin A to show a modified ability to bind to MHC class II antigens.

* * * * *

```
                          SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (xi) SEQUENCE DESCRIPTION: SEQ ID NO:1:

Gly  Gly  Ala  Ala  His  Tyr  Gly
                    5
```